United States Patent [19]

Pytlewski et al.

[11] 4,337,368

[45] Jun. 29, 1982

[54] REAGENT AND METHOD FOR DECOMPOSING HALOGENATED ORGANIC COMPOUNDS

[75] Inventors: Louis L. Pytlewski; Kenneth Krevitz, both of Philadelphia, Pa.; Arthur B. Smith, Littleton, Colo.

[73] Assignee: The Franklin Institute, Philadelphia, Pa.

[21] Appl. No.: 158,359

[22] Filed: Jun. 11, 1980

Related U.S. Application Data

[63] Continuation-in-part of Ser. No. 142,865, Apr. 21, 1980.

[51] Int. Cl.$^3$ ............................................. C07C 39/12
[52] U.S. Cl. .................................. 568/730; 568/717; 568/770; 568/774; 568/796; 568/802; 570/204; 570/220
[58] Field of Search ............... 568/730, 770, 774, 796, 568/717; 585/802, 712; 570/204, 205, 226, 230, 220

[56] References Cited

U.S. PATENT DOCUMENTS

| | | | |
|---|---|---|---|
| 1,996,744 | 4/1935 | Britton | 260/154 |
| 2,448,092 | 8/1948 | Gibson | 585/802 |
| 2,449,088 | 9/1948 | Smith | 260/396 |
| 2,914,558 | 11/1959 | Cooper | 568/796 |
| 3,075,021 | 1/1963 | Luvisi et al. | 570/204 |
| 3,188,357 | 6/1965 | Blumbergs | 570/224 |
| 3,243,464 | 3/1966 | Parvi et al. | 260/620 |
| 3,413,341 | 11/1968 | Bursack et al. | 260/521 |
| 3,595,931 | 7/1971 | Hays et al. | 570/204 |
| 3,686,337 | 8/1972 | Chang | 260/650 |
| 4,001,340 | 1/1977 | Smith et al. | 260/620 |

FOREIGN PATENT DOCUMENTS

| | | | |
|---|---|---|---|
| 1930341 | 6/1969 | Fed. Rep. of Germany | 568/730 |
| 49-82570 | 8/1974 | Japan . | |
| 618189 | 2/1949 | United Kingdom | 570/226 |
| 1045298 | 10/1966 | United Kingdom | 568/796 |
| 1221019 | 2/1971 | United Kingdom | 568/796 |

OTHER PUBLICATIONS

W. H. Dennis et al., Bulletin of Environmental Contamination & Toxicology, vol. 14, No. 6, pp. 736–744 (1975).

A. Oku et al., Chemistry and Industry, pp. 841 and 842 (Nov. 1978).

P. Johncock et al., Analytical Chemistry, vol. 94, pp. 245–247 (1959).

Liggett, Analytical Chemistry, vol. 26, No. 4, pp. 748–750 (1954).

*Primary Examiner*—Werren B. Lone
*Attorney, Agent, or Firm*—Dann, Dorfman, Herrell and Skillman

[57] ABSTRACT

A reagent, comprising the product of the reaction of an alkali metal with a polyglycol or a polyglycol monoalkyl ether and oxygen, effects complete decomposition of halogenated organic compounds, such as polychlorinated biphenyls (PCBs), when mixed therewith in the presence of oxygen.

23 Claims, No Drawings

REAGENT AND METHOD FOR DECOMPOSING HALOGENATED ORGANIC COMPOUNDS

This application is a continuation-in-part of U.S. patent application Ser. No. 142,865, filed Apr. 21, 1980, in the names of Louis L. Pytlewski, Kenneth Krevitz and Arthur B. Smith.

BACKGROUND OF THE INVENTION

The present invention relates generally to a composition of matter and to the use of said composition in a method for decomposing hazardous halogen-containing organic compounds, such as polychlorinated biphenyls.

The potential hazard to public health and the environment posed by the indiscriminate disposal of a variety of synthetic halogen-containing organic chemicals is well known. Compounds such as polychlorinated biphenyls (PCBs), dichlorodiphenyltrichloroethane (DDT), decachlorooctahydro-1,3,4-metheno-2H-cyclobuta-[c,d]-pentalen-2-one (Kepone®), and 2,4,5-trichlorophenoxyacetic acid, (2,4,5-T), although having demonstrated utility, have been found in recent years to be persistent environmental poisons, and, therefore, require a safe and effective means of disposal.

The difficulty encountered in attempting to dispose of halogenated organic compounds is due in large measure to the highly stable nature of the carbon-halogen bonds present therein. The bond energy of a carbon-chlorine bond, for example, is on the order of eighty-four kcal./mole. These compounds are not only resistant to biodegradation, they cannot be degraded in a practical and effective manner by any of the well-known chemical decomposition methods. Thus, although chemical decomposition of halogen-containing organic compounds, including PCBs, has been reported, the methods employed, such as chlorolysis, catalyic dehydrohalogenation, molten salt reactions, ozone reactions, and alkali metal reduction, possess one or more significant limitations. For example, these prior art methods typically require expensive reagents, inert atmospheres, extensive temperature control, complex apparatus, substantial energy consumption, and the like. The principal problem with these methods is that they achieve incomplete dehalogenation. The impracticability of the aforementioned prior art disposal methods is evidenced by the fact that none has gained widespread acceptance by government or industry.

Incineration has also been employed as a means for disposal of hazardous chemicals but it too has certain notable drawbacks. In the first place, it requires substantial energy consumption. Hence, the expense involved in this method of disposal will probably steadily increase. Secondly, incineration requires the use of complex equipment to remove corrosive and/or toxic substances from the incinerator effluent. Thus, the expense of constructing an incineration disposal facility makes it uneconomical for those having a hazardous chemical waste disposal problem who might advantageously employ a practical disposal system. Thirdly, the residual ash formed during incineration may be toxic and present a further disposal problem.

Only a few incineration facilities are currently in operation, and some of these are in remote locations, adding excessively high transportation costs to the cost of disposal in many cases.

PCBs pose a particularly serious disposal problem. Once widely used as dielectric fluid additives in electrical equipment such as transformers and capacitors because of their excellent insulating properties, the use of PCBs were banned recently by the United States Environmental Protection Agency (E.P.A.) due to their cumulative storage in human fatty tissue and reports of extremely high toxicity. In connection with the ban, the E.P.A. has promulgated a rule whereby the available means of effective decomposition of extant PCBS and PCB-contaminated substances is limited to incineration. However, incineration of PCB-contaminated materials in accordance with E.P.A.-approved procedures is decidedly wasteful since potentially recyclable materials, such as dielectric and hydraulic fluids, which may contain a relatively small amount of PCBs are destroyed in the process. To avoid such waste, it has been proposed to treat recyclable materials contaminated by PCBs with an absorbent, e.g., by passing the material through a bed of activated charcoal or a resin to selectively remove the PCBs from said material. Although PCBs are physically removed from the recyclable material in this manner, the disposal of absorbed PCBs still remains a problem.

Aside from the PCB disposal problem, there are significant quantities of other waste or excess halogen-containing organic chemicals presently being held in storage by manufacturers, processors or consumers, which chemicals must be disposed of eventually in an environmentally acceptable manner. Viewed realistically, storage of toxic chemicals can only be considered a stopgap measure while efforts to develop a safe, practical and effective process for their disposal continue. Storage capacity is finite, whereas the amount of hazardous chemical substances generated by industry is estimated to increase by about three percent annually.

It is apparent that a need exists for an effective and efficient process for the decomposition of halogenated organic compounds, and preferably one that is capable of (1) scavenging the hazardous substances from materials contaminated therewith, thus permitting reuse of said materials, and (2) converting the hazardous substances to useful products.

SUMMARY OF THE INVENTION

The aforementioned deficiencies of the prior art methods for disposing of halogenated organic compounds have been overcome in accordance with the present invention wherein a halogenated organic compound is decomposed by the steps of reacting an alkali metal, a suitable liquid reactant, such as a polyglycol or a polyglycol monoalkyl ether, and oxygen to form a decomposition reagent, and adding a halogenated compound, or mixture of halogenated compounds, to the decomposition reagent in the presence of oxygen to achieve decomposition thereof.

The present invention is particularly useful for the decomposition of chlorinated organic compounds and results in complete and rapid cleavage of the carbon-chlorine bond. At elevated temperatures, the dehalogenation reaction goes to completion in less than 5 minutes. Moreover, the reagents used in carrying out the method are relatively inexpensive and only relatively unsophisticated equipment is required. Both of these factors are significant from the standpoint of application of the method on a commercial scale.

Aside from providing a practical and effective means for the disposal of halogenated organic compounds that are uncontaminated with other substances, e.g., "neat" PCBs, the present invention makes it possible to "scavenge", from otherwise useful materials, halogenated organic compounds that are dissolved in relatively small amounts in those materials. For example, the present invention may be used to remove chlorine from PCB-contaminated dielectric fluids. Further, the present invention is at once capable of decomposing halogenated organic compounds and producing useful products which are readily recoverable from the reaction medium.

DESCRIPTION OF THE INVENTION

In accordance with the present invention, it has been discovered that the products of the reaction of molten alkali metals with certain liquid reactants, such as polyglycols or polyglycol monoalkyl ethers, and oxygen provide reagents capable of decomposing a host of halogenated organic compounds. When halogenated organic compounds, such as PCBs, are added to this reagent in the presence of oxygen, dehalogenation occurs quickly and completely.

As a practical matter, because of handling problems the alkali metals particularly suitable for practicing the present invention are sodium, lithium and potassium or the amalgams of these metals. Of these, sodium is the preferred metal due to its high reactivity and relatively low cost.

The liquid reactants that may be utilized in carrying out the present invention, have the general formula

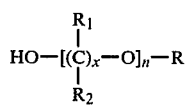

wherein R is hydrogen or lower-alkyl, $R_1$ and $R_2$ are the same or different and are selected from the group consisting of hydrogen, unsubstituted or substituted lower alkyl, unsubstituted or substituted cycloalkyl having from 5 to 8 carbon atoms, and unsubstituted or substituted aryl, n has a value from about 2 to about 400, and x has a value of at least 2, which includes polyglycols and polyglycol monoalkyl ethers. The lower alkyl radical in the foregoing formula may be methyl, ethyl, propyl, butyl, isobutyl, etc. The cycloalkyl radical may be cyclopentyl, cyclohexyl, cycloheptyl an cyclooctyl. The aryl radical may be phenyl, benzyl, biphenyl, naphthyl, etc. The substituents on the $R_1$ and $R_2$ radicals include, but are not limited to, lower-alkyl, e.g. methyl, ethyl, propyl, butyl, isobutyl etc.; halo, e.g., chloro, bromo; nitro; sulfato; carboxyl; amino; mono- and di-lower-alkylamino, e.g. methylamino, ethylamino, dimethylamino, methylethylamino; amido; hydroxy, lower alkoxy, e.g. methoxy, ethoxy, etc.

Suitable liquid reactants falling within the above formula include diethylene glycol, diethylene glycol monomethyl ether, polyether glycols, such as polyethylene glycols, polypropylene glycols, and polybutylene glycol and related long chain glycol monoalkyl ethers. The preferred liquid reactants are those of the above general formula wherein $R_1$ and $R_2$ are hydrogen and x is 2. Particularly preferred are polymers of polyethylene glycol having the formula HO$\pm$CH$_2$—CH$_2$—O$\pm_n$H wherein n may have a value between about 2 and about 400. These polymers have an average molecular weight range from about 100 to about 20,000. Neither low volatility, non-polar liquids, nor glycolic liquids in which both terminal hydroxyl groups are alkylated has been found to produce the desired decomposition.

The term "polyglycols", as used herein, is intended to signify polymers of dihydric alcohols.

In preparing the decomposition reagent, the alkali metal and liquid reactant are mixed together, preferably with stirring. The mixture may be heated to accelerate the rate of reaction of the metal with the liquid. The extent of heating required will vary depending on the particular metal and liquid used. In the case of a decomposition reagent formed from sodium and a polyethylene glycol having an average molecular weight of 400, for example, heating of the mixture to a temperature in the range of about 50° C. to about 80° C. gives a satisfactory reaction rate. Upon heating, the reaction becomes exothermic and the temperature of the reaction mixture rises to near or above the melting point of the sodium, which is 97.6° C. With the rise in temperature, the sodium becomes molten and reaction with the liquid ensues. Alkali metals having lower melting points may undergo reaction with the liquid after initial mixing at room temperature.

Oxygen is a necessary reactant in the formation of the decomposition reagent. When air is present, for example, the alkali metal and the liquid react vigorously with the evolution of hydrogen gas. When reaction occurs, the reaction mixture takes on a deep amber color. This color change is distinct and readily observable. Attempts to carry out the reaction of sodium with polyethylene glycol in an oxygen-free atmosphere have produced only sodium glycolate and hydrogen. The resultant solution is virtually clear and is ineffective as a decomposition reagent. However, it has been found that when sodium and polyethylene glycol are reacted in an atmosphere consisting essentially of nitrogen, and oxygen is thereafter introduced into the resultant sodium glycolate solution, the decomposition reagent will be formed, as indicated by the aforementioned color change. Thus, the alkali metal, liquid reactant and oxygen, may be reacted simultaneously, or according to the two-step procedure just described. The two-step procedure is advantageous in that it avoids having hydrogen and oxygen present simultaneously in the reaction system, thereby avoiding a potential explosion hazard. Furthermore, it lessens the possibility that inactive by-products will be formed.

Once formed, the decomposition reagent may be used immediately, or it may be stored for later use. In general, the reagent may be stored for at least six months without significantly diminishing its reactivity.

In order to achieve decomposition of a halogenated organic compound in accordance with this invention, all that is necessary is to add the compound to the decomposition reagent in the presence of oxygen and heat the mixture to obtain a reasonable rate of reaction. It has been determined that the use of pure oxygen enhances the rate of dehalogenation by a factor of five. Efforts to dechlorinate PCBs in an inert atmosphere, such as dry nitrogen, using a decomposition reagent formed from sodium and polyethylene glycol have been unsuccessful. As for the extent of heating required for dehalogenation, a temperature of about 40° C. to about 180° C. has been found to produce satisfactory results. The temperature will vary depending upon the nature of the decomposition reagent used and the halogenated organic compound being decomposed.

Although the reaction mechanism underlying the present invention has not been completely elucidated, studies of the decomposition of PCBs using a reagent comprising sodium and polyethylene glycol having an average molecular weight of 400 have shed some light on the mechanism involved.

As a result of these studies, the following reaction sequence has been postulated, in which R signifies the radical —CH$_2$—O—CH$_2$]$_9$—CH$_2$OH and X signifies a PCB residue of the general formula

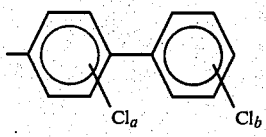

wherein a=1 to 5 and b=1 to 5.

A. The reaction of sodium and polyethylene glycol (avg. M.W. 400) proceeds with the formation of a sodium glycolate and the evolution of hydrogen according to the reaction:

B. The sodium glycolate disproportionates in a state of equilibrium in accordance with the reaction:

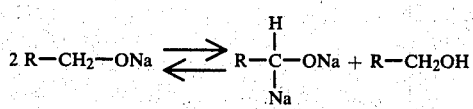

C. Oxygen insertion between sodium-carbon bonds occurs:

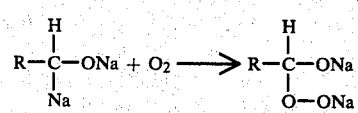

D. The product of the oxygen insertion reaction decomposes into a pair of free radicals:

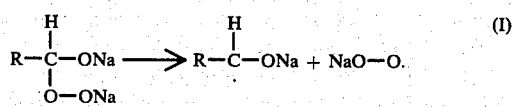

E. Free radical (I) reacts with free oxygen:

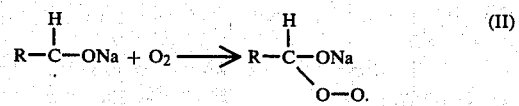

F. The chlorine carbon bonds in PCB's, are attacked by free radical (II):

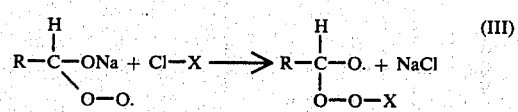

G. Free radical (III) reacts with additional sodium glycolate:

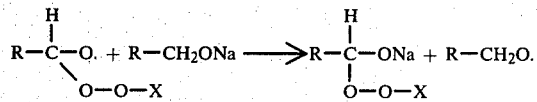

H. The peroxy derivative produced in the preceding reaction decomposes to form a hydroxylated biphenyl and the sodium salt of a derivative of glycolic acid.

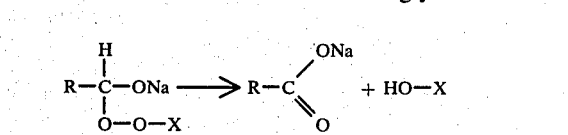

Consideration had been given the possibility that polyethylene glycol may undergo the well-known insertion reaction with oxygen to form hydroperoxides in accordance with the following generalized equation:

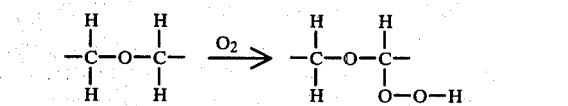

This possibility was discounted, however, when it was discovered that this reaction does not readily occur with polyethylene glycol. When polyethylene glycol is first reacted with sodium, however, as represented in reaction A, the reaction of the sodium glycolate with oxygen occurs readily, as represented in reaction B. It is this reaction that is believed to produce the aforementioned color change. Thus, it appears that the rapid oxygen uptake that has been observed is due in part to a reaction that occurs only with polyglycols or polyglycol monoalkyl ethers by insertion of oxygen between sodium-carbon bonds. The oxygen of the ether linkages in polyglycols and polyglycol monoalkyl ethers is believed to give rise to an inductive effect which promotes the oxygen insertion reaction shown in B.

Solutions resulting from the reaction of sodium with polyethylene glycol (avg. M.W. 400) have been found to give a strong electron spin resonance (E.S.R.) absorption band located at 3,391 gauss, having a narrow band width of 7 gauss. This E.S.R. spectrum matches that observed for the superoxide ion, O$_2^-$. Notwithstanding that the decomposition reagent may contain such a highly reactive species, the superoxide ion is not believed to be the principal reactive species responsible for the dehalogenation of halogen-containing organic compounds that has been achieved by the method. Such a hypothesis does not account for the continuous supply of oxygen required in practice for the decomposition reaction to occur. It has been noted that when the reaction of sodium and polyethylene glycol is allowed to proceed only to the stage at which the superoxide ion is produced, i.e., reaction D, and PCBs are added to the reaction mixture in the absence of oxygen, no dehalogenation occurs. Dehalogenation has been found to result only when additional oxygen is present. This indicates that some species other than the superoxide ion is the active species in the dehalogenation reaction, and has led to the conclusion that the complex sodium glycolate-superoxide radical (II) formed in reaction E, above, is the key species responsible for dehalogenation.

The other free radicals formed in the foregoing sequence, including the superoxide ion of reaction D, are believed to be too stable in the reaction medium to have a significant effect on the dehalogenation reaction per se.

From the foregoing reaction sequence, it can be seen that the process of the present invention produces relatively innocuous products, the principal ones being sodium chloride, and polyhydroxylated aromatics. Hydrogen is also generated as a result of the initial reaction of the alkali metal with the liquid reactant. It should be noted that the formation of sodium chloride in step E above is considered the principal driving force for the overall reaction sequence.

Polyhydroxylated biphenyls containing as many as eight hydroxyl groups may be formed as products of the method described herein. As a class, these polyhydroxylated biphenyls include compounds which are potentially useful as reactants in the production of polymers, as plasticizers, as anti-oxidants, and as solvents for high temperature reactions. These compounds are readily recoverable from the reaction medium by conventional separation techniques, such as solvent extraction. Considering that the useful products formed during the process may be marketed, at least part of the operating costs of the instant method should be recoverable.

Standard safety precautions must be exercised in practicing this invention due to the evolution of hydrogen gas which occurs. Thus, the use of an open flame or exposed electrical heating elements must be avoided. Further, since alkali metals are employed in forming the decomposition reagent, it is suggested that a safe heating source be used if heating is utilized in preparing the decomposition reagent. Other standard precautions for working with alkali metals must also be taken.

The order in which the steps of the decomposition method are carried out is not considered critical. Thus, while a presently preferred order has been described hereinabove, the method may be practiced otherwise. For example, the halogen-containing organic compound may be added to the liquid reactant in the presence of oxygen prior to the addition of the alkali metal. Further, the alkali metal and the halogenated organic compound may be added simultaneously to the liquid reactant. Alternatively, the alkali metal and halogen-containing organic compound may be added to the liquid reactant in an oxygen-free atmosphere, e.g. pure nitrogen, with subsequent introduction of oxygen into the reaction mixture to form the decomposition reagent, whereby complete dechlorination of the halogenated compound is rapidly achieved.

The invention will be further understood by reference to the following examples.

EXAMPLE I—PREPARATION OF DECOMPOSITION REAGENT AND DECHLORINATION OF A PCB OIL (AROCHLOR 1254)

A sodium polyethylene glycol reagent (referred to in these examples as NaPEG) was prepared by placing 900 ml of polyethylene glycol, having an average m.w. of 400 (referred to in these examples as PEG 400) in a 3000 ml beaker and heating until the temperature approached 80° C. Stirring was accomplished by using an efficient overhead mechanical stirrer or a magnetic stirring assembly. Thereafter, approximately 55 grams of freshly cut sodium metal was added, all within a two minute period.

CAUTION: If the sodium metal is added over an extended period of time the possibility of a sodium fire may exist.

Within ten minutes, the temperature of the mixture rose to about 120° C. and was maintained as close as possible to this value, until all the sodium, which melted and formed a shiny layer on top of the solvent, had reacted. Reaction is evidenced by the change of color of the PEG 400 to a dark amber and the disappearance of the shiny metal layer. If all of the sodium does not react, small additions of PEG 400 may be used to effect complete reaction. Alternatively, the NaPEG mixture may be placed in a separatory funnel and the lower NaPEG layer drawn off. The unreacted sodium metal will rise to the top and may be decomposed by reaction with methanol.

Dechlorination was carried out by heating 25 g of the NaPEG reagent prepared above to 100° C. and adding thereto exactly 10.00 ml of a 1000 ppm Inerteen ® in cyclohexane standard. Inerteen ® is a commercial polychlorinated biphenyl (PCB) oil manufactured by Westinghouse, Inc. At this temperature the cyclohexane boiled off immediately, leaving the PCB in intimate contact with the NaPEG. After 10 minutes reaction time, a 4 ml aliquot was withdrawn from the reaction system and then added to 5 ml of distilled water and stirred vigorously for three minutes. After complete solution of the NaPEG aliquot in water, 5 ml of reagent grade cyclohexane was added to the aqueous system and stirred again for three minutes.

After the two phases separated, the organic layer was analyzed for its Inerteen concentration via gas chromatography with an electron capture detector, preceded by a Florosil column clean-up step. The experimental conditions for the gas chromatographic analysis were as follows: Injection port temperature, 200° C.; Detector temperature, 200° C.; Column temperature, 200° C.; Isothermal scan; Scan time, 20 minutes; Carrier gas, 10% methane in argon; Carrier gas flow rate, 40 ml/minute; Column packing, 1.5% OV-17 and 1.95% QF-1 on 80/100 mesh GasChrom Q.

Gas chromatographic analyses showed the concentration of Inerteen remaining after the ten minute reaction time to be less than 50 parts per billion (ppb).

In all dehalogenation reactions using the NaPEG reagent, a common reaction product is a sodium halide, which in the case of dechlorination is specifically sodium chloride. After reaction, a 5 ml aliquot of the reaction medium was added to 50 ml of water and tested for water soluble $Cl^-$ using a $Cl^-$ selective electrode. The analysis showed that the PCB had been dehalogenated to the extent of 97%±3%.

The $Cl^-$ selectivity was tested for possible interferences using aliquots of fresh NaPEG reagent in water. The $Cl^-$ selective electrode was unresponsive and therefore the NaPEG system itself was free of interferences. The rate of appearance of water soluble $Cl^-$ may be used to do precise kinetics measurements on this system.

A confirmatory test for the formation of water soluble $Cl^-$ in NaPEG dechlorination reactions was conducted whereby aliquots of the reaction mixtures were acidified with 0.3 M $HNO_3$, aqeous Ag $NO_3$ added, and AgCl precipitated. The AgCl residues were analyzed using SEM techniques and found to be pure.

EXAMPLE II—ALTERNATE PREPARATION OF DECOMPOSITION REAGENT

The NaPEG reagent was also prepared in accordance with the following two-step method. In the first step, 900 ml of PEG 400 and 55 grams of sodium were placed in a three-neck round bottom flask (2000 ml), which was continually flushed with nitrogen gas and heated to a temperature of 80° C. Stirring was accomplished by using an efficient overhead mechanical stirrer. A magnetic stirring assembly may also be used. Since there is no oxygen present in the reaction vessel, the possibility of a sodium fire is greatly reduced when following this procedure. Hydrogen was evolved as a result of the reaction between the dissolved sodium and the PEG 400. At this point, the reaction mixture was essentially colorless. No reaction was observed when a PCB oil was added to the reaction mixture. When air was introduced into the reaction mixture, a rapid reaction occurred as evidenced by the color change to dark amber described in Example I, thus indicating that the NaPEG reagent had been formed.

EXAMPLE III—DECHLORINATION OF PCB'S IN HYDROCARBON-BASED TRANSFORMER OILS

The NaPEG reagent was prepared in the same manner as set forth in Example I. One quart of hydrocarbon-based transformer oil, contaminated with approximately 1000 ppm of PCB's, was heated to 100° C. in a two liter beaker. Thereafter, 25 grams of NaPEG reagent were added to the oil sample and stirred vigorously, using an overhead mechanical stirrer or a magnetic stirring assembly.

After 1 hour reaction time, the reaction mixture was allowed to cool to room temperature and then was added to a 4000 ml separatory funnel equipped with either a glass or Teflon stopcock. To help ensure complete transfer of the oil sample, small (25 ml or less) portions of a 1 N NaOH solution may be used to rinse the beaker. To extract products of the dechlorination reaction, 1 liter of 1 N NaOH was added to the separatory funnel which was then stoppered and shaken vigorously for five minutes, venting excess pressure buildup as necessary. The aqueous layer was drawn off and discarded and the extraction procedure with NaOH was repeated with a fresh 1 liter sample of aqueous base. Extractions were repeated until the aqueous layer showed no visible dark coloration after extraction. This will generally require 3-5 extractions with fresh NaOH solution.

After disposal of all aqueous extracts, the transformer oil, which is usually turbid, was dried and clarified by passing through a column of 5 Angstrom molecular sieves. The molecular sieves were packed in a glass tube fitted with a stopcock or other means of regulating eluant flow rate. The dimensions of the glass column were approximately 1 inch inside diameter by 19 inches in length. The column was prepared by placing a small wad of glass wool in the bottom of the tube and then placing a 14 inch bed of molecular sieves atop the glass wool. The oil sample was dried by simply pouring it through the column and collecting the eluant in a clean, dry flask. The rate of elution should not exceed 2 drops per second, or the sample will not be effectively dried. In addition, the first 50-75 ml of eluant will have to be re-added to the system to complete the drying procedure, because the initial amount of oil added to the column will pass through very quickly and will not be efficiently contacted by the molecular sieves.

The concentration of PCBs remaining in the dried transformer oil was determined by removing a 10 ml sample of oil, adding it to an equal volume of pure PEG 400, and stirring vigorously for three minutes. The PCBs were extracted into the PEG 400 layer and were further extracted by removing the PEG 400 layer and adding it to 10 ml of reagent grade cyclohexane. After stirring vigorously for five minutes, the two layers were allowed to separate and the cyclohexane layer was analyzed by gas chromatography as described in Example I. The results showed residual PCB to be present in a concentration of less than 50 ppb.

This example shows that the method of this invention may be used effectively to scavenge PCBs from recyclable materials contaminated therewith.

EXAMPLE IV—DECHLORINATION OF "NEAT" PYRANOL (AROCHLOR 1248) USING NaPEG REAGENT

Pyranol, another type of commercial PCB oil, was dechlorinated in a manner essentially identical to that described in Example I. For every gram of pyranol dechlorinated, approximately 5 grams of NaPEG reagent were required. The pyranol in this case was added neat, i.e., not diluted in an organic solvent. Preparation of the NaPEG reagent, dechlorination procedure, and post-reaction analyses were carried out in a manner identical to those described in Example I. The analyses showed that the chlorine content of the pyranol had been reduced by about 97%±3%.

EXAMPLE V—DECHLORINATION OF PURE HEXACHLOROBENZENE USING NaPEG REAGENT

Hexachlorobenzene was dechlorinated in a procedure essentially identical to that described in Example I. The only exceptions were that hexachlorobenzene was added neat and that the weight ratio was four grams of NaPEG reagent per gram of hexachlorobenzene dechlorinated. Gas chromatographic analyses showed the hexachlorobenzene to be essentially completely dechlorinated, with residual concentrations of 50 ppb or less.

EXAMPLE VI—DECHLORINATION OR TRICHLOROBENZENE ISOMERS USING NaPEG REAGENT

The various isomeric trichlorobenzenes were investigated because they can make up as much as 50% of the composition of industrial PCB oils. They have been dechlorinated in a manner essentially identical to that described in Example I. The only differences were that the trichlorobenzenes were added to the reagent neat and that approximately three grams of NaPEG were required for each gram of trichlorobenzene dechlorinated. In the gas chromatographic analyses, the scan time for the chromatogram can be reduced to approximately five minutes, owing to the low polarity and molecular weights of the isomeric trichlorobenzenes. Analysis, using a $Cl^-$ selective electrode showed that the chlorine content of the trichloroenzenes had been reduced by about 97%.±3%.

EXAMPLE VII—DECHLORINATION OR HEXACHLOROCYCLOHEXANE USING NaPEG REAGENT

Pure hexachlorocyclohexane was dechlorinated using the procedures of Example I. 10 mls of a 1000 ppm solution of hexachlorocyclohexane in cyclohexane was added to the NaPEG reagent. Analysis of using a $Cl^-$ selective electrode showed that the chlorine content of the hexachlorocyclohexane had been reduced by about 97%.

EXAMPLE VIII—DECHLORINATION OF KEPONE USING NaPEG REAGENT

Kepone ® was dechlorinated using the procedures of Example 1. Kepone ® was dissolved in a 15% (by vol) acetone-cyclohexane mixture to the extent of 1000 ppm. 10 ml of this solution was added to the NaPEG reagent. Gas chromatographic analyses showed the Kepone to be substantially completely dechlorinated.

EXAMPLE IX—DECOMPOSITION OF CHLOROETHYLETHYLSULFIDE USING NaPEG REAGENT

The procedures of Example 1 were applied to 5 ml of neat chloroethylethylsulfide (a "Mustard gas" model compound). The compound was completely dechlorinated, and the carbon-sulfur bond cleaved. The reaction products were determined to be NaCl, $Na_2S$, and ethanol.

EXAMPLE X—DECHLORINATION OF DDT USING NaPEG REAGENT

DDT, dichlorodiphenyltrichlorethane, was treated using the procedures of Example 1. 10 ml of a 1000 ppm cyclohexane solution of DDT in cyclohexane was added to the NaPEG reagent and complete dechlorination occurred in less than 10 minutes, as determined by gas chromatography/electron capture techniques.

Procedures similar to those set forth above have been followed for the dehalogenation of tetrachlorobenzene and pentachlorophenol.

Although the method of the present invention has been exemplified with reference to the decomposition of specific halogenated organic compounds, the process may be used with success for the decomposition of a wide variety of other halogen-containing organic compounds. Mixtures of organic halogenated compounds other than PCBs may also be decomposed by this method.

Those skilled in the art will appreciate that the method disclosed in the foregoing examples is merely illustrative and is capable of wide variation and modification without departing from the scope of the invention as defined in the appended claims.

We claim:

1. A method for the decomposition of a halogenated organic compound, comprising the steps of:
   (a) providing a reaction mixture comprising the halogenated compound, a reactant having the general formula

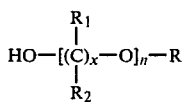

wherein R is hydrogen or lower alkyl, $R_1$ and $R_2$ are the same or different and are selected from the group consisting of hydrogen, unsubstituted or substituted lower alkyl, unsubstituted or substituted cycloalkyl having from 5 to 8 carbon atoms, and unsubstituted or substituted aryl, n has a value of from 2 to about 400, and x has a value of at least 2, and an alkali metal; and
   (b) reacting said reactant with said alkali metal and oxygen to form a decomposition reagent, which effects substantially complete removal of halogen from said halogenated compound and forms an oxygenated derivative of said compound.

2. The method claimed in claim 1 wherein the alkali metal is selected from the group consisting of sodium, potassium, and amalgams thereof, and $R^1$ and $R^2$ in the general formula are hydrogen, x is 2, and n has a value between 3 and 440.

3. The method claimed in claim 2 wherein the halogenated organic compound is selected from the group consisting of hexachlorocyclohexane, hexachlorobenzene, trichlorobenzene, tetrachlorobenzene, pentachlorophenol, dichlorodiphenyltrichloroethane, decachlorooctahydro-1,3,4-mehteno-2H-cyclobuta-pentalen-2-one and polychlorinated biphenyl.

4. A method for the decomposition of a halogenated organic compound, comprising the steps of:
   (a) providing a reaction mixture comprising the halogenated compound, a reactant having the general formula

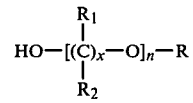

wherein R is hydrogen or lower alkyl, $R_1$ and $R_2$ are the same or different and are selected from the group consisting of hydrogen, unsubstituted or substituted lower alkyl, unsubstituted or substituted cycloalkyl having from 5 to 8 carbon atoms, and unsubstituted or substituted aryl, n has a value of from 2 to about 400, and x has a value of at least 2, and an alkali metal;
   (b) reacting said reactant with said alkali metal in a substantially oxygen-free atmosphere to produce an intermediate product; and (c) reacting oxygen with the intermediate product produced in step b to form a decomposition reagent which effects substantially complete removal of halogen from said halogenated compound and forms an oxygenated derivative of said compound.

5. The method claimed in claim 4 wherein the substantially oxygen-free atmosphere consists essentially of nitrogen.

6. The method claimed in claim 4 wherein the alkali metal is selected from the group consisting of sodium, potassium, and amalgams thereof, and $R^1$ and $R^2$ in the general formula are hydrogen, x is 2, and n has a value between 3 and 400.

7. The method claimed in claim 6 wherein the halogenated organic compound is selected from the group consisting of hexachlorocyclohexane, hexachlorobenzene, trichlorobenzene, tetrachlorobenzene, pentachlorophenol, dichlorodiphenyltrichloroethane, decachlorooctahydro-1,3,4-metheno-2H-cyclobuta-pentalen-2-one and polychlorinated biphenyl.

8. A method for the decomposition of a halogenated organic compound, comprising the steps of:

(a) providing a decomposition reagent formed by reacting an alkali metal, a reactant having the general formula:

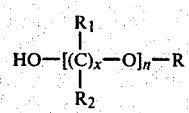

wherein R is hydrogen or lower alkyl, $R_1$ and $R_2$ are the same or different and are selected from the group consisting of hydrogen, unsubstituted or substituted lower alkyl, unsubstituted or substituted cycloalkyl having from 5 to 8 carbon atoms, and unsubstituted or substituted aryl, n has a value from about 2 to about 400 and x has a value of at least 2, and oxygen; and (b) reacting said decomposition reagent with said halogenated organic compound in the presence of oxygen to effect substantially complete dehalogenation of said halogenated organic compound and form an oxygenated derivative of said compound.

9. The method claimed in claim 8 wherein said decomposition reagent is produced from an alkali metal selected from the group consisting of sodium, potassium, and amalgams thereof, and a liquid reactant of the above general formula wherein $R^1$ and $R^2$ are hydrogen, x is 2, and n has a value between 3 and 400.

10. The method claimed in claim 9 wherein the halogenated organic compound is selected from the group consisting of hexachlorocyclohexane, hexachlorobenzene, trichlorobenzene, tetrachlorobenzene, pentachlorophenol, dichlorodiphenyltrichloroethane, decachlorooctahydro-1,3,4-metheno-2H-cyclobuta-pentalen-2-one and polychlorinated biphenyl.

11. A method for the decomposition of a polychlorinated biphenyl, comprising the steps of:
(a) providing a decomposition reagent formed by reacting an alkali metal, a reactant having the general formula:

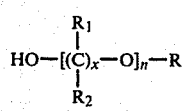

wherein R is hydrogen or lower alkyl, $R_1$ and $R_2$ are the same or different and are selected from the group consisting of hydrogen, unsubstituted or substituted lower alkyl, unsubstituted or substituted cycloalkyl having from 5 to 8 carbon atoms, and unsubstituted or substituted aryl, n has a value from about 2 to about 400 and x has a value of at least 2, and oxygen; and (b) reacting said decomposition reagent with said polychlorinated biphenyl in the presence of oxygen to effect substantially complete dehalogenation of said halogenated organic compound and form an oxygenated derivative of said compound.

12. The method claimed in claim 11 wherein said decomposition reagent is produced from sodium and polyethylene glycol.

13. A method for the decomposition of a polychlorinated biphenyl, comprising the steps of:
(a) providing a reaction mixture comprising the polychlorinated biphenyl, a reactant having the general formula

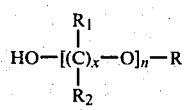

wherein R is hydrogen or lower alkyl, $R_1$ and $R_2$ are the same or different and are selected from the group consisting of hydrogen, unsubstituted or substituted lower alkyl, unsubstituted or substituted cycloalkyl having from 5 to 8 carbon atoms, and unsubstituted or substituted aryl, n has a value of from 2 to about 400, and x has a value of at least 2, and an alkali metal; and (b) reacting said reactant with said alkali metal and oxygen to form a decomposition reagent which effects substantially complete removal of halogen from said polychlorinated biphenyl and forms an oxygenated derivative of said compound.

14. The method claimed in claim 13 wherein the alkali metal is sodium and the liquid is polyethylene glycol.

15. A method for the decomposition of a polychlorinated biphenyl, comprising the steps of:
(a) providing a reaction mixture comprising the polychlorinated biphenyl, a reactant having the general formula

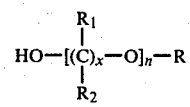

wherein r is hydrogen or lower alkyl, $R_1$ and $R_2$ are the same or different and are selected from the group consisting of hydrogen, unsubstituted or substituted lower alkyl, unsubstituted or substituted cycloalkyl having from 5 to 8 carbon atoms, and unsubstituted or substituted aryl, n has a value of from 2 to about 400, and x has a value of at least 2, and an alkali metal;

(b) reacting said reactant with said alkali metal in a substantially oxygen-free atmosphere to produce an intermediate product; and (c) reacting oxygen with the intermediate product produced in step b to form a decomposition reagent which effects substantially complete removal of halogen from said polychlorinated biphenyl and forms an oxygenated derivative of said compound.

16. The method claimed in claim 15 wherein the alkali metal sodium and the liquid is polyethylene glycol.

17. A method for the decomposition of a chlorinated organic compound comprising the steps of:
(a) reacting sodium, polyethylene glycol and oxygen at a temperature of from about 80° C. to about 120° C. to form a decomposition reagent; and
(b) adding the chlorinated compound to the decomposition reagent in the presence of oxygen and heating to about 100° C. to effect substantially complete dechlorination of the chlorinated compound and form an oxygenated derivative of said compound.

18. A method for the decomposition of a chlorinated organic compond comprising the steps of:
(a) mixing the chlorinated compound with polyethylene glycol;

(b) reacting the polyethylene glycol with sodium in a substantially oxygen-free atmosphere at a temperature of from about 80° C. to about 120° C.; and (c) reacting oxygen with the reaction products of step b and heating the reaction mixture to about 100° C. to effect substantially complete dechlorination of the chlorinated compound and form an oxygenated derivative of said compound.

19. The method claimed in claim 18 wherein the substantially oxygen-free atmosphere consists essentially of nitrogen.

20. The method claimed in claim 15 wherein the substantially oxygen-free atmosphere consists essentially of nitrogen.

21. A method for the decomposition of a polychlorinated biphenyl, comprising the steps of:

(a) reacting sodium, polyethylene glycol and oxygen at a temperature of from about 80° C. to about 120° C. to form a decomposition reagent; and (b) adding the polychlorinated biphenyl to the decomposition reagent in the presence of oxygen and heating to about 100° C. to effect substantially complete dechlorination of the polychlorinated biphenyl and form an oxygenated derivative thereof.

22. A method for the decomposition of a polychlorinated biphenyl comprising the steps of:

(a) providing a reaction mixture comprising the polychlorinated biphenyl, polyethylene glycol and sodium;

(b) reacting said polyethylene glycol with said sodium in a substantially oxygen-free atmosphere at a temperature of from about 80° C. to about 120° C.; and (c) reacting oxygen with the reaction products of step b and heating the reaction mixture to about 100° C. to effect substantially complete dechlorination of the polychlorinated biphenyl and form an oxygenated derivative thereof.

23. The method claimed in claim 22 wherein the substantially oxygen-free atmosphere consists essentially of nitrogen.

* * * * *

UNITED STATES PATENT AND TRADEMARK OFFICE
CERTIFICATE OF CORRECTION

PATENT NO. : 4,337,368
DATED : June 29, 1982
INVENTOR(S) : Louis L. Pytlewski, Kenneth Krevitz, Arthur B. Smith It is certified that error appears in the above-identified patent and that said Letters Patent are hereby corrected as shown below:

Claim 2, line 5, "440" should be --400--.

Claim 3, line 6, "chlorooctahydro-1,3,4-mehteno-2H-cyclobuta-pental-" should be --chlorooctahydro-1,3,4-metheno-2H-cyclobuta-[c,d]-pental- --.

Claim 7, line 6, after "cyclobuta-" insert --[c,d]--.

Claim 10, line 6, after "cyclobuta-" insert --[c,d]--.

Claim 12, line 1, "11" should be --9--.

Claim 14, line 1, "13" should be --2--.

Claim 16, line 1, "15" should be --6--;
line 2, after "metal" insert --is--.

Signed and Sealed this

Eighth Day of February 1983

[SEAL]

Attest:

GERALD J. MOSSINGHOFF

Attesting Officer    Commissioner of Patents and Trademarks